(12) United States Patent (10) Patent No.: US 7,862,699 B2
Barron et al. (45) Date of Patent: Jan. 4, 2011

(54) MATRIX AND DYNAMIC POLYMER SYSTEMS AND COMPOSITIONS FOR MICROCHANNEL SEPARATION

(75) Inventors: Annelise E. Barron, Evanston, IL (US); Cheuk Wai Kan, Medford, MA (US); Christopher P. Fredlake, Chicago, IL (US)

(73) Assignee: Northwestern University, Evanston, IL (US)

( * ) Notice: Subject to any disclaimer, the term of this patent is extended or adjusted under 35 U.S.C. 154(b) by 1038 days.

(21) Appl. No.: 11/591,915

(22) Filed: Nov. 1, 2006

(65) Prior Publication Data

US 2007/0108055 A1 May 17, 2007

Related U.S. Application Data

(60) Provisional application No. 60/732,398, filed on Nov. 1, 2005.

(51) Int. Cl.
*G01N 27/447* (2006.01)
*G01N 27/453* (2006.01)
(52) U.S. Cl. .................. 204/455; 204/605; 204/469
(58) Field of Classification Search ............... 204/450, 204/455, 469, 600, 605
See application file for complete search history.

(56) References Cited

U.S. PATENT DOCUMENTS 6,787,016 B2 * 9/2004 Tan et al. .............. 204/455

2003/0087290 A1 5/2003 Tarlov
2005/0000569 A1 1/2005 Bousse et al.

OTHER PUBLICATIONS

Albarghouthi, MN; Buchholz, BA; Doherty, EAS; Bogdan, FM; Zhou, H; and Barron, AE; Impact of Polymer Hydrophobicity on the Properties and Performance of DNA Sequencing Matrices for Capillary Electrophoresis; Electrophoresis, 2001, 737-747, vol. 22, Wiley-VCH Verlag GmbH, 69451 Weinheim.

Albarghouthi, MN; Buchholz, BA; Huiberts, PJ; Stein, TM; and Barron, AE; Poly-N-hydroxyethlacrylamide (polyDuramide): A Novel, Hydrophilic, Self-Coating Polymer Matrix for DNA Sequencing by Capillary Electrophoresis; Electrophoresis, 2002, 1429-1440, vol. 23, Wiley-VCH Verlag GmbH, 69451 Weinheim.

Albarghouthi, MN; Stein, TM; and Barron, AE; Poly-N-hydroxyethylacrylamide as a Novel, Adsorbed Coating for Protein Separation by Capillary Electrophoresis; Electrophoresis, 2003, 1166-1175, vol. 24, Wiley-VCH Verlag GmbH & Co, KGaA Weinheim.

Barron, AE; Sunada, WM; and Blanch, HW; The Effects of Polymer Properties on DNA Separations by Capillary Electrophoresis in Uncross-linked Polymer Solutions; Electrophoresis, 1996, 744-757, vol. 17, VCH Verlagsgesellschaft mbH, 69451 Weinheim.

(Continued)

*Primary Examiner*—Kaj K Olsen
(74) *Attorney, Agent, or Firm*—Reinhart Boerner Van Deuren s.c.

(57) ABSTRACT

Matrix polymers and dynamic coating polymers, compositions thereof and related methods, systems and apparatus for microchannel separation.

35 Claims, 4 Drawing Sheets

OTHER PUBLICATIONS

Barron, AE; Blanch, HW; and Soane, DS; A Transient Entanglement Coupling Mechanism for DNA Separation by Capillary Electrophoresis in Ultradilute Polymer Solutions; Electrophoresis, 1994, 597-615, vol. 15, VCH Verlagsgesellschaft mbH, 69451 Weinheim.

Chiari, M; Riva, S; Gelain, A; Vitale, A; and Turati, E; Separations of DNA Fragments by Capillary Electrophoresis in N-substitued Polyacrylamides; Journal of Chromatography A, 1997, 347-355, vol. 781, Elsevier Science B.V.

Doherty, EAS; Berglund, KD; Buchholz, BA; Kourkine, IV; Przybycien, TM; Tilton, RD; and Barron, AE; Critical Factors for High-performance Physically Adsorbed (dynamic) Polymeric Wall Coatings for Capillary Electrophoresis of DNA; Electrophoresis, 2002, 2766-2776, vol. 23, Wiley-VCH Verlag GmbH & Co. KGaA, Weinheim.

Duke, Taj; Semenov, AN; and Viovy, JL; Mobility of a Reptating Polymer; Physical Review Letters, Nov. 30, 1992, 3260-3263, vol. 69, The American Physical Society.

Duke, T; Vioy, JL and Semenov, AN; Electrophoretic Mobility of DNA in Gels. I. New Biased Reptation Theory Including Fluctuations; Biopolymers, 1994, 239-247, vol. 34, John Wiley & Sons, Inc.

Grossman, PD and Soane, DS; Experimental and Theoretical Studies of DNA Separations by Capillary Electrophoresis in Entangled Polymer Solutions; Biopolymers, 1991, 1221-1228, vol. 31, John Wiley & Sons, Inc.

Heller, C; Finding a Universal Low Viscosity Polymer for DNA Separation (II); Electrophoresis, 1998, 3114-3127, vol. 19, Wiley-VCH Verlag GmbH, 69451 Weinheim.

Heller, C; Influence of Electric Field Strength and Capillary Dimensions on the Separation of DNA; Electrophoresis, 2000, 593-602, vol. 21, Wiley-VCH Verlag GmbH, 69451 Weinheim.

Heller, C; Duke, T; and Viovy, JL; Electrophoretic Mobility of DNA in Gels II. Systematic Experimental Study in Agarose Gels, Biopolymers, 1994, 249-259, vol. 34, John Wiley & Sons, Inc.

Liu, S; Ren, H; Gao, Q; Roach, DJ; Loder JR, RT; Armstrong, TM; Mao, Q; Blaga, I; Barker, DL; and Jovanovich, SB; Automated Parallel DNA Sequencing on Multiple Channel Microchips; PNAS, May 9, 2000, 5369-5374, vol. 97, No. 10, National Academy of Sciences.

Liu, S; Shi, Y; JA, WW; and Mathies, RA; Optimization of High-Speed DNA Sequencing on Microfabracated Capillary Electrophoresis Channels; Analytical Chemistry, Feb. 1, 1999, 566-573, vol. 71, No. 3, American Chemical Society.

Lumpkin, OJ; Dejardin, P; and Zimm, BH; Theory of Gel Electrophoresis of DNA; Biopolymers, 1985, 1573-1593, vol. 24, John Wiley & Sons, Inc.

Lunney, J; Chrambach A; and Rodbard, D; Factors Affecting Resolution, Band Width, Number of Theoretical Plates, and Apparent Diffusion Coefficients in Polyacrylamide Gel Electrophoresis; Analytical Biochemistry, 1971, 158-173, vol. 40.

Madabhushi, R; Separation of 4-color DNA Sequencing Extension Products in Noncovalently Coated Capillaries Using Low Viscosity Polymer Solutions; Electrophoresis, 1998, 224-230, vol. 19, Wiley-VCH Verlag GmbH, 69451 Weinheim.

Paegel, BM; Emrich, CA; Wedemayer, GJ; Scherer, JR; and Mathies, RA; High Throughput DNA Sequencing with a Microfabricated 96-lane Capillary Array Electrophoresis Bioprocessor; PNAS, Jan. 22, 2002, 574-579, vol. 99, No. 2, National Academy of Sciences.

Rodbard, D and Chrambach, A; Unified Theory for Gel Electrophoresis and Gel Filtration; Proceedings of the National Academy of Sciences, Apr. 1970, 970-977, vol. 65, No. 4.

Salas-Solano, O; Schmalzing, D; Koutny, L; Buonocore, S; Adourian, A; Matsudaira, P; and Ehrlich, D; Optimization of High-Performance DNA Sequencing on Short Microfabricated Electrophoretic Devices; Analytical Chemistry, Jul. 15, 2000, 3129-3137, vol. 72, American Chemical Society.

Slater, GW and Noolandi, J; On the Reptation Theory of Gel Electrophoresis; Biopolymers, 1986, 431-454, vol. 25, John Wiley & Sons, Inc.

Viovy, JL and Duke, T; DNA Electrophoresis in Polymer Solutions: Ogston Sieving, Reptation and Constraint Release; Electrophoresis, 1993, 322-329, vol. 14, VCH Verlagsgesellschaft mbH, D-6940 Weinheim.

Woolley, AT and Mathies, RA; Ultra-High-Speed DNA Sequencing Using Capillary Electrophoresis Chips; Analytical Chemistry, Oct. 15, 1995, 3676-3680, vol. 67, No. 20, American Chemical Society.

Wyatt, PJ; Light Scattering and the Absolute Characterization of Macromolecules; Analytica Chimica Acta, 1993, 1-40, vol. 272, Elsevier Science Publishers B.V., Amsterdam.

Yamaguchi, Y; Todorov, TI; Morris, MD; and Larson, RG; Distribution of single DNA Molecule Electrophoretic Mobilities in Semidilute and Dilute Hydroxyethylcellulose Solutions; Electrophoresis, 2004, 999-1006, vol. 25, Wiley-VCH Verlag GmbH & Co. KGaA, Weinheim.

De Carmejane, O; Yamaguchi, Y; Todorov, TI; and Morris, MD; Three-dimensional Observation of Electrophoretic Migration of dsDNA in Semidilute Hydroxy-ethylcellulose Solution; Electrophoresis, 2001, 2433-2441, vol. 22, Wiley-VCH Verlag GmbH, 69451 Weinheim.

Barron, AE; Soane, DS; and Blanch, HW; Capillary Electrophoresis of DNA in Uncross-linked Polymer Solutions; Journal of Chromatography A, 1993, 3-16, vol. 652, Elsevier Science Publishers B.V., Amsterdam.

* cited by examiner

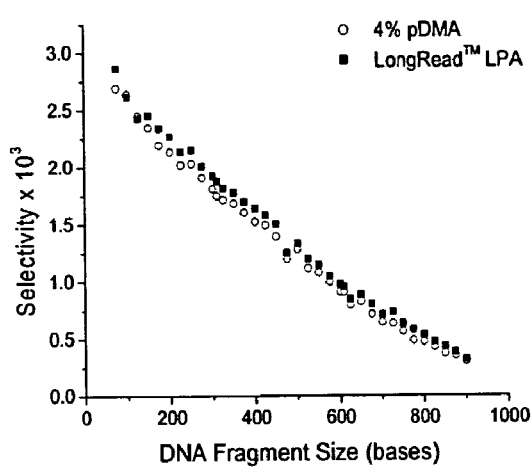
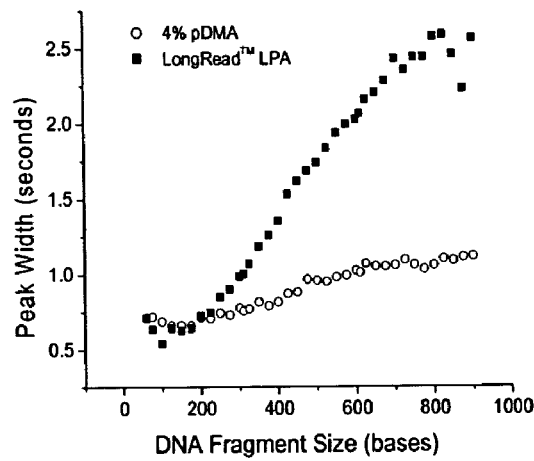
FIGURE 4A　　　　　　　　　　　FIGURE 4B
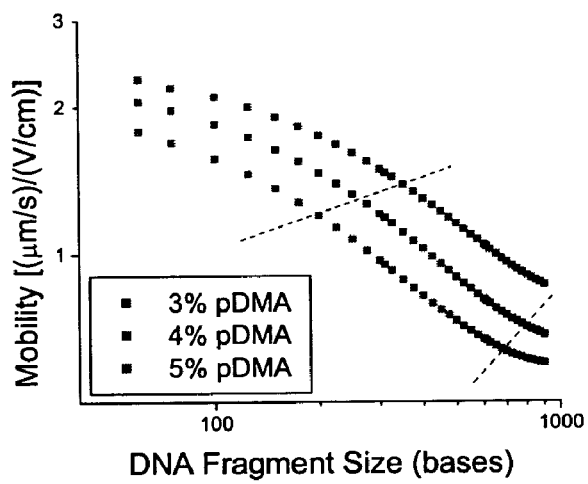
FIGURE 5

US 7,862,699 B2

MATRIX AND DYNAMIC POLYMER SYSTEMS AND COMPOSITIONS FOR MICROCHANNEL SEPARATION

This invention claims priority benefit from application Ser. No. 60/732,398 filed Nov. 1, 2005, the entirety of which is incorporated herein by reference.

The United States government has certain rights to this invention pursuant to Grant Nos. 1 R01 HG 019770-01 and DMR-0076097 from the National Institutes of Health and the National Science Foundation, respectively, to Northwestern University.

BACKGROUND OF THE INVENTION

Microfluidic chip-based electrophoresis for DNA sequencing represents the future for high-throughput sequencing projects due to reductions in cost, time and reagent consumption and the possibility of integrating sequencing with other steps of genetic analysis into a total micro-analytical system. To this end, the development of optimal polymeric separation matrices and wall coatings for DNA sequencing on microfluidic chips is crucial.

Hydrophilic separation matrices, e.g., linear polyacrylamides ("LPA"), have been used along with covalent hydrophilic coatings to achieve read lengths greater than 500 bases by microchannel electrophoresis; however, the separations have all taken greater than 15-18 minutes. Poly(N,N-dimethylacrylamide) ("pDMA") is a hydrophobic separation matrix that due to the hybrid separation mechanism achieves similar read lengths as polymers of the prior art but in much faster times. While covalent coatings have been used almost exclusively for all published microchannel DNA sequencing results, dynamic coatings, being much less expensive and also much easier to implement, are greatly preferred for the microchannel format. However, all dynamic coatings demonstrated for DNA sequencing have been somewhat hydrophobic leading to loss of separation efficiency due to interactions of the DNA fragments and the wall coatings. Previous work has shown that poly(N-hydroxyethylacrylamide) ("pHEA") is a suitable hydrophilic dynamic coating for capillaries for both protein separation and DNA sequencing, but only when pHEA is also the separation matrix. While most published data on microchip-based DNA sequencing have reported read lengths of greater than 400 bases, sequencing times on chips generally have ranged from 18-30 minutes. And, capillary electrophoresis requires about 60-90 minutes to give comparable results. Time and read length considerations present ongoing concerns in the art relating to electrophoretic separations.

SUMMARY OF THE INVENTION

In light of the foregoing, it is an object of the present invention to provide one or more polymeric compositions, systems and/or methods for use in microchannel separation, thereby overcoming various deficiencies and shortcomings of the prior art, including those outlined above. It will be understood by those skilled in the art that one or more aspects of this invention can meet certain objectives, while one or more aspects can meet certain other objectives. Each objective may not apply equally, in all its respects, to every aspect of this invention. As such, the following objects can be viewed in the alternative with respect to any one aspect of this invention.

It can be an object of the present invention to provide a dynamic wall coating polymer to better employ the advantages associated with hydrophobic separation matrices.

It can be another object of the present invention to provide, alone or in conjunction with the preceding objective, a hydrophilic wall coating polymer to reduce the incidence or effect of electroosmotic flow and/or analyte-wall interactions.

It can be another object of the present invention to provide a matrix/wall coating system, together with related methods of use, to increase sequence read lengths over shorter times as compared to the prior art.

It can be another object of the present invention to provide one or more matrix/wall coating systems affording longer, quicker sequence reads, flow microchannel electrophoresis.

Other objects, features, benefits and advantages of the present invention will apparent from this summary and the following descriptions of certain embodiments, and will be readily apparent to those skilled in the art of various electrophoretic methods and techniques. Such objects, features, benefits and advantages will be apparent from the above as taken in conjunction with the accompanying examples, data, figures and all reasonable inferences to drawn therefrom.

The present invention relates to a novel system that can enable ultra-fast DNA sequencing or genotyping by microchip electrophoresis under an applied electric field, with a relatively short separation channel. Such a system can comprise a polymeric separation component and a polymeric coating component. In certain embodiments, a DNA separation matrix comprising a high-molecular weight poly(N,N-dimethylacrylamide) (PDMA) or a copolymer thereof, can be used in conjunction with a hydrophilic water-soluble polymer component, poly(N-hydroxyethylacrylamide) (pHEA), to provide extraordinarily fast separation of DNA sequencing fragments by microchannel electrophoresis. Without limitation, pHEA can be considered a dynamic (i.e., physically adsorbed) polymer wall coating component. It can be pre-coated on a microchannel wall and/or provided as part of a composition comprising a polymeric separation matrix component. In certain other embodiments, such a system or composition of this invention can comprise such separation and coating components at molecular weights and/or in amount(s) sufficient to provide a novel mode of DNA migration i.e., a novel DNA separation mechanism that combines DNA reptation with transient entanglement coupling (TEC).

More generally, in part, the present invention can be directed to a DNA sequencing or genotyping composition for microchannel electrophoresis. Such a composition can comprise a hydrophobic separation matrix component comprising a polyacrylamide of a formula $\text{-[CH}_2\text{C(R)C(O)NR'R"]}_n$ wherein R can be selected from H and methyl, and R' and R" can be independently selected from $C_1$ to about $C_8$ linear alkyl moieties, $C_1$ to about $C_8$ alkoxy-substituted linear alkyl moieties, $C_1$ to about $C_8$ branched alkyl moieties, and $C_1$ to about C8 alkoxy-substituted branched alkyl moieties, copolymers thereof, and combinations of such polymers and/or copolymers; and a hydrophobic wall coating component comprising a poly(N-hydroxyethylacrylamide), more hydrophilic than such a matrix component.

Whether a homopolymer, random or block copolymer, or in any such combination, in certain embodiments, R can be H and R' and R" can comprise a $C_1$ to about $C_4$ alkyl moiety, whether substituted (e.g., methoxy or ethoxy, propoxy, etc.) or unsubstituted. In certain other embodiments, R' and R" can be methyl, and such a component can comprise pDMA or a pDMA copolymer. With respect to such a formula, n is an integer greater than 1 corresponding to the average molar mass of such a polymer. In certain embodiments, such a polymer can be moderately hydrophobic, as would be understood in the art, and at least partially soluble in water or an aqueous medium. Accordingly, such components can comprise pDMA, poly(N-methoxyethylacrylamide) or poly(N-ethoxyethylacrylamide), combinations thereof, as well as copolymers thereof with respect to monomers corresponding to any one or more of the polymeric components described or inferred herein (e.g., without limitation, a copolymer of N,N-dimethylacrylamide and N,N-dihexylacrylamide). Regardless, any combination of R' and R" is limited only by hydrophobic character imparted to such a polymeric component and ability to, either intra- or intermolecularly, physically interact and/or associate with other such moieties or polymeric components to an extent at least partially sufficient to provide a functional effect of the sort described more fully below.

Such a hydrophilic wall coating component can be considered in the context of hydrophilic character sufficient to at least partially reduce electroosmotic flow and/or reduce deleterious analyte-wall interactions. pHEA can have a molecular weight ranging from about 600,000 to about 4 million g/mol (MDa) or to about 5 million g/mol (MDa) or more. Regardless, depending upon molecular weight and/or end-use application, pHEA can be present in a fluid medium at less than 0.5% (w/v) of the medium. In certain other embodiments, pHEA can be present at about 0.1 to about 0.4% (w/v) in such a medium (e.g. aqueous) as would be understood by those skilled in the art. Regardless, certain embodiments, a pHEA coating component can also be used compositionally in conjunction with or added to one or more of the aforementioned hydrophobic polyacrylamide separation matrix components.

Regardless, the resulting matrix component can be present in a composition comprising a fluid medium, of the sort described herein, e.g., in water or an aqueous medium (e.g., without limitation, a buffer solution), in a concentration at a percent (w/v) ranging up to about 5% or greater, such a concentration as can depend upon average molar mass. In certain embodiments, up to about 3% (w/v) of such a matrix component can comprise pDMA, with a weight average molar mass ranging from about 3 to about 5 MDa. In other such embodiments, the matrix component can comprise an additional about 1% to about 2% (w/v) of a pDMA, with a lower weight average molar mass, e.g., without limitation, ranging from about 200 to about 300 kDa. Various other matrix components are available, over a range of concentrations, determined and limited only by choice of monomeric component(s) and corresponding moieties.

Unless otherwise indicated, all numbers expressing properties such as molar mass, percent and the like, used herein, are to be understood as being modified in all instances by the term "about". Accordingly, unless indicated to the contrary, the numerical parameters herein are approximations that can vary depending upon desired polymer or system properties or results to be achieved using any methods relating thereto, such percentages and molar masses as can be varied by those skilled made aware of this invention.

With respect to any of the compositions, systems, methods and/or apparatus of the present invention, the polymers described or inferred herein can suitably comprise, consist of or consist essentially of any of the aforementioned monomers, regardless of the percent of any such monomer in any corresponding polymer. Each such polymeric or copolymeric compound or monomeric component thereof is compositionally distinguishable, characteristically contrasted and can be practiced in conjunction with the present invention, separate and apart from another. Accordingly, it should also be understood that the inventive compositions, systems, methods and/or apparatus, as illustratively disclosed herein, can be practiced or utilized in the absence of any one polymer, monomeric component and/or step which may or may not be disclosed, referenced or inferred herein, the absence of which may not be specifically disclosed, referenced or inferred herein.

In part, the present invention can also be directed to a microchannel electrophoresis system for RNA and DNA separations. Such a system can comprise a hydrophobic separation matrix component comprising a pDMA and a hydrophilic wall coating component comprising a pHEA; and a microchannel substrate selected from a micro dimensioned capillary (e.g., without limitation, defining an internal diameter ranging from about 10 microns to about 150 microns), or a microfluidic electrophoresis chip with a similar such microchannel dimension. Such a system can comprise a pDMA matrix component of the sort described above. In certain non-limiting embodiments, the matrix component can comprise about 3% (w/v) pDMA with a weight average molar mass ranging from about 3 to about 5 MDa; and about 1% to about 2% (w/v) pDMA, with a lower weight average molar mass (e.g., one ranging from about 200 to about 300 kDa).

In part, the present invention can also be directed to a method of using a polymeric wall coating and separation matrix system for either electrophoretic DNA or RNA separation. Such a method can comprise providing a system comprising a pDMA component comprising about 3% (w/v) to about 5% (w/v) of such a system, and a pHEA component; introducing the system to a substrate of the sort selected from a microchannel electrophoresis capillary and a microfluidic sequencing chip; and contacting a mixture of either a DNA sequencing reaction product or a RNA component with the system, at an applied voltage and for a time at least partially sufficient for eletrophoretic separation. Such a method can comprise a system comprising a pDMA component of the sort described above. In certain embodiments, the pHEA component can be contacted with the substrate prior to introduction of the separation matrix system. In such embodiments, the pHEA component can be used as an aqueous solution, contacting the substrate for a time sufficient to provide a wall coating component of the sort described herein. Regardless, such a method can be used to separate DNA sequences (e.g., single-strand DNA) of length up to about 800 bases, such separation depending upon time and microchannel length. Non-limiting examples of such a separation/sequencing methodology are provided below.

As can relate to the preceding, this invention can also be directed to a microchannel electrophoresis apparatus. Such an apparatus can comprise a substrate and a polymeric system thereon, with such a substrate selected from a micron-dimensioned capillary and a microfluidic electrophoresis chip. Without limitation to microchannel substrate, or apparatus configuration, such a system can comprise a polymeric system comprising a pDMA component comprising about 3% to about 5% (w/v) of such a system and pHEA component of the sorts described above. Such polymeric systems have demonstrated separation and/or wall-coating performance, and can also be used in conjunction or combination with other types of capillary or microchannel matrix or wall coating materials known in the art.

In part, this invention can also be directed to a method of using a hydrophobic polymer matrix to enhance DNA separations speed. Such a method can comprise providing a microchannel substrate selected from a micro-dimensioned capillary and a microfluidic electrophoresis chip; coupling or applying a hydrophilic pHEA wall coating component to such a substrate; introducing a hydrophobic separation matrix to the substrate, such a matrix component selected from the polyacrylamides described herein, copolymers thereof and combinations of such polyacrylamides and/or such copolymers; and contacting a mixture of DNA sequence components and such a matrix component, at an applied voltage and for a time at least partially sufficient for electrophoretic separation of such a mixture, the matrix component(s) of a molecular weight and at a concentration at least partially sufficient for at least one of transient entanglement coupling and reptation of the DNA components within the mixture. In certain embodiments, separation can be a combination of transient entanglement coupling and reptation. In certain such embodiments, the DNA components can migrate by transient entanglement coupling about 50% of the migration time and by reptation about 50% of the migration time. Regardless, such migration dynamics can be monitored by epifluorescent videomicroscopy of fluorescently stained DNA molecules. In certain embodiments, such a method can provide separation up to about 3 times faster, compared to separations using LPA matrices of the prior art.

Without limitation, in certain embodiments, the matrix component of such a methodology can be selected from pDMA and/or copolymers thereof. With regard to the former, such a matrix component can comprise about 3% (w/v) pDMA, with a weight average molar mass ranging from about 3 to about 5 MDa, and about 1% (w/v) to about 2% (w/v) pDMA, with a lower weight average molar mass, e.g., one ranging from about 200 to about 300 kDa. Regardless, in such embodiments, migration can be characterized by a linear region of a log-log plot of DNA electrophoretic mobility versus DNA molecular size through the matrix, where molecular size can be gauged in terms of bases and/or base pairs. For instance, without limitation, a DNA molecular size range can be from about 200 bases to about 800 bases, with the linear region of such a log-log plot having a slope between about −4.40 and −0.60.

BRIEF DESCRIPTION OF THE DRAWINGS

FIGS. 4A-B. A) The selectivities ($\mu_i$-$\mu_{i-1}$/$\mu_{avg}$) of the peaks from the separation in FIG. 2. Both matrices show similar peak separations. B) The peaks in the LongRead™ matrix get much wider than in the pDMA matrix past 250 bases. (This band broadening is a major cause of lower sequencing performance of this matrix.)

FIG. 5. Mobility data for ssDNA ladder in pDMA matrices. Conditions are the same as in FIG. 1. The dashed lines mark the DNA sizes where the plot is linear. Slopes of the linear region are −0.54, −0.59, and −0.50 for the 3%, 4%, and 5% matrices, respectively.

DETAILED DESCRIPTIONS OF CERTAIN EMBODIMENTS

Figure 1:
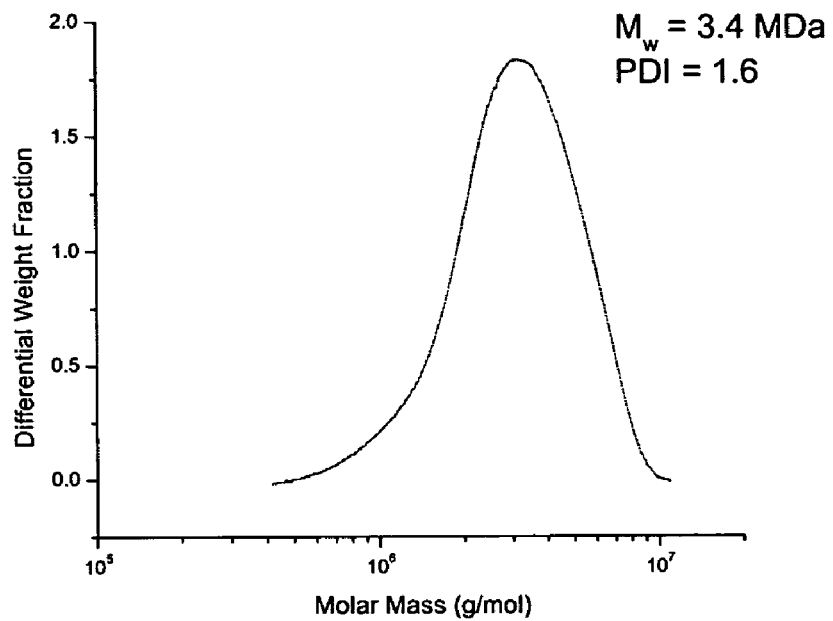
FIG. 1. Characterization of pDMA by GPC-MALLS. Molar mass distribution of pDMA used in several non-limiting examples. The distribution is an average of three runs.

Entangled polymer solution properties that can influence DNA separations in electrophoresis.

To further understand certain embodiments of this invention, consider the following: Developing optimal polymer matrices for sequencing is one of the greatest limitations for commercializing microchannels systems. DNA sequencing is only possible in semi-dilute polymer solutions where the polymer chains overlap and form and entangled network. The overlap concentration, c*, is defined as the bulk solution concentration that exactly matches the concentration of the polymer inside a coil. Equation 1 provides an estimate of c* based on this definition $$c^* \approx \frac{3M_w}{4\pi N_A R_g^3} \tag{1}$$

where $M_w$ is the weight average-molar mass, $N_A$ is Avagadro's number, and $R_g$ is the polymer radius of gyration. From Eq (1), the overlap concentration can be calculated by measuring both the $M_w$ and $R_g$ by techniques such as light scattering. Alternatively, the overlap concentration can be determined by measuring the zero-shear viscosity of a series of polymer concentrations and plotting viscosity versus polymer concentration on a log-log scale. The concentration where the plot becomes non-linear is the overlap concentration the extent at which the network is entangled can be expressed as the c/c* ratio.

As DNA moves through entangled polymer networks, the critical parameter for defining the network is the polymer screening length, ξ. For polymer solutions, the screening length is dependent on polymer $R_g$ and concentration $$\xi = 0.5 R_g \left(\frac{c}{c^*}\right)^{\frac{-3}{4}} \tag{2}$$

In gel electrophoresis, the average pore size was critical for determining separation mechanism and in an attempt to connect the theories regarding separation mechanism from gels to entangled networks. It has been proposed to use the screening length as a "pore size" in these solutions, with this view altered slightly by defining the "blob" size, $\xi_b$, as the average chain length between entanglement points. This adjustment only introduced a new prefactor in the definition and is defined as $$\xi_b = 2.86\xi = 1.43 R_g \left(\frac{c}{c^*}\right)^{\frac{-3}{4}} \tag{3}$$

Thus, the polymer network in general can be defined in terms of this blob size which depends on both polymer concentration and coil size.

DNA separation mechanisms in entangled polymer solutions.

The polymer network parameters described above can be used to describe the different mechanisms of DNA migration through the entangled network. The mechanism for separation depends on the $R_g$ of the DNA molecules relative to the size of the blobs in the network. DNA sizes smaller than the pore size of the network migrate through the solution by a mechanism similar to one described by Ogston for spheres moving though a dense array of fibers. This is generally referred to as Ogston sieving and the mobility of DNA relative to the free solution mobility can be described mathematically by $$\frac{\mu}{\mu_0} = \exp(-K_r c) \tag{4}$$

where $K_r$ is the retardation coefficient which is proportional to the square of the DNA coil radius and c is the gel or polymer concentration. This mechanism is analyzed by Ferguson plots which plot the natural log of the analyte mobility versus the gel of polymer concentration. The slope of the line, then, gives the value for the retardation coefficient.

The Ogston model for DNA mobility would be expected to fail as the coil size of DNA molecules approach and surpass the pore size of the network. The observation that DNA larger than the pore size led to the biased reptation model for DNA mobility. This model was re-evaluated by taking into account that the length of the DNA molecule is subject to fluctuations and named biased reptation with fluctuations. These models predict that the mobility of DNA snakes through the network similar to the reptation theory for entangled polymer melts of solutions. A critical parameter in this mechanism is the reduced electric field and this is given by $$\varepsilon = \frac{\eta_s \xi_b \mu_0 E}{k_b T} \tag{5}$$

where $\eta_s$ is the solvent viscosity, E is the electric field strength, $k_b$ is Boltzmann's constant, and T is the absolute temperature. These models were generally derived for instances of low fields, or $\varepsilon \ll 1$. The resulting form of the mobility for the BRF model is given by $$\left(\frac{\mu}{\mu_0}\right)_{BRF} = \left[(3N)^{-2} + \left(\frac{2\varepsilon}{5+2\alpha\varepsilon}\right)^2\right]^{\frac{1}{2}} \tag{6}$$

where N is the DNA size in bases and $\alpha$ is an adjustable factor. For this model a critical DNA size exists for which DNA sizes below the first term dominates and DNA mobility is size dependent.

$$\left(\frac{\mu}{\mu_0}\right) = \frac{1}{3N} \text{ for } N < N_{crit} \tag{7}$$

This regime of DNA reptation is known as unoriented reptation and most DNA separations including sequencing is carried out in this regime. For DNA above the critical size, the second term dominates and size based separation vanishes. This regime of reptation is known as oriented reptation. The critical size of DNA depends on both pore size and electric field strength.

$$N_{crit} \sim \varepsilon^{-2} \tag{8}$$

The critical size is predicted to be independent of mesh size, but prior work showed that the transition from un-oriented to oriented reptation depends on mesh size. Such results show that smaller pore sizes tend to shift oriented reptation to smaller DNA sizes. So the electric field strength as well as the blob size of the entangled network are critical parameters in determining the upper limit for DNA size based separation by electrophoresis.

While the mechanisms of Ogston sieving and biased reptation are applicable to entangled solutions, Barron et al. discovered a different separation mechanism prevalent in polymer solutions below the overlap concentration. In ultra-dilute solutions of hydroxyethlycellulose (HEC) separation of large dsDNA molecules (>1 kbp) was possible and that the theories for entangled polymer solutions were inadequate to explain the results. Therefore, a new mechanism termed transient entanglement coupling was proposed to account for the separation. In this mechanism, the DNA encounters the polymer chains during migration and the coupling of the two increases the drag on the DNA molecule. The probability of encountering polymer chains is DNA size dependent and thus separation is possible.

Figure 2:
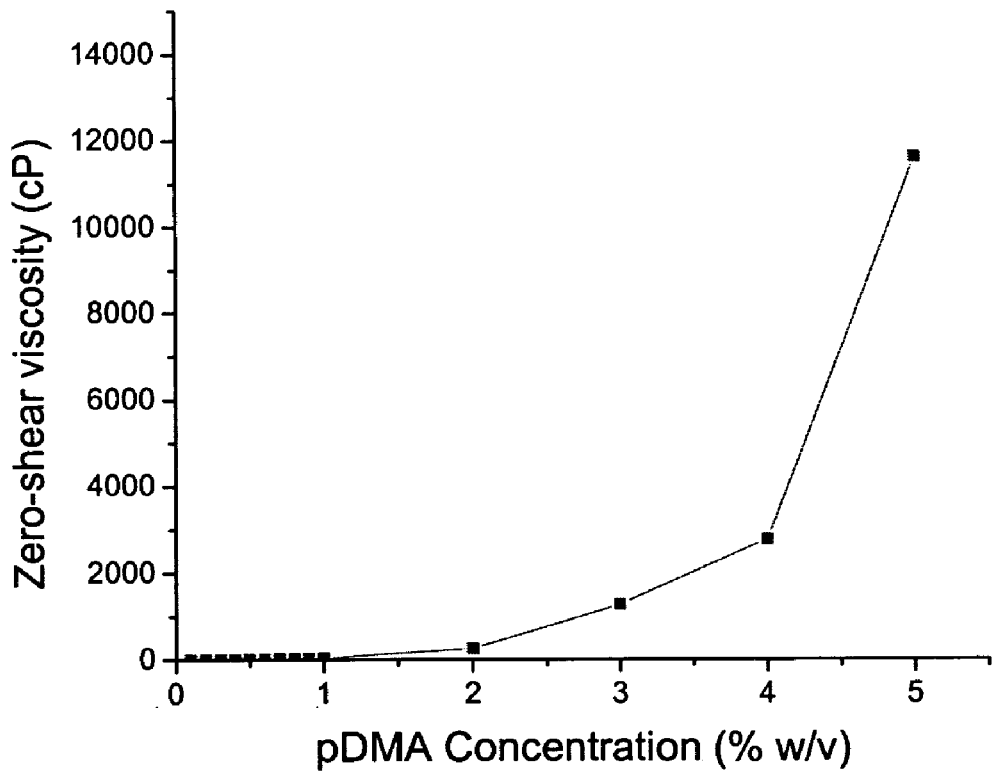
FIG. 2. The viscosity of pDMA matrices increase dramatically at concentrations suitable for sequencing. However, the viscosity is still much lower than LPA matrices, of the prior art, for easier microchannel loading.

Polymer physical properties have an impact on sequencing performance. Generally, hydrophilic, high molar mass polymers are needed for longer DNA sequencing read lengths. At the same time, lower viscosities and the ability to coat a glass surface provide technical and cost advantages to operating the system. The synthesis conditions targeted pDMA and pHEA molar masses in excess of $1 \times 10^6$ g/mol. Typically this is the threshold to provide longer DNA sequencing reads while also meeting the requirement for a stable dynamic coating. FIG. 1 displays the molar mass distribution for the pDMA used in this study as measured by GPC-MALLS. Polymer properties measured at room temperature for pDMA and pHEA are summarized in Table 1. The zero-shear viscosity of pDMA solutions are shown in FIG. 2. Many LPA matrices have viscosities on the order of 100,000 cP[28] pDMA matrices in the concentration range useful for sequencing will be much easier to load into microchannels.

TABLE 1

| Polymer properties of pDMA and pHEA synthesized for matrix and coating | | | |
|---|---|---|---|
| Polymer | $M_w$ (MDa) | $R_g$ (nm) | PDI |
| pDMA | 3.4 | 124 | 1.6 |
| pHEA | 4.0 | 135 | 3.2 | ssDNA Separations

Although pDMA has been explored as an effective sequencing matrix in capillary electrophoresis instruments, this polymer has not been tested for sequencing in microchannel systems. Separation of ssDNA fragments was carried out in a microchannel electrophoresis system using the pDMA in concentrations from 3-5% along with a commercial LPA matrix as a control. The sample is a 25 base ladder containing 37 DNA fragment sizes. The electropherograms from these separations are presented in FIG. 3. While the 3% and 4% pDMA matrices are able to separate all 37 peaks, the 5% pDMA and the LPA matrices do not fully resolve the largest DNA fragments. So in addition to having lower viscosities, pDMA solutions separate a 25 base ladder up to 900 bases better than a 4% LPA matrix. The effective separation distance in this system is 7.5 cm, much less than in commercial CAE instruments. Since microchannel systems employ a cross injector design that enables a much more efficient separation, the required channel length is greatly reduced and thus the separation is faster.

For the pDMA matrices, a dependence of DNA migration times on the polymer concentration is evident, and migration times are generally shorter for these pDMA matrices than the LPA matrix. Since most microchannel sequencing studies have also used longer channels as well as different electric field strengths and temperatures in an effort to optimize their individual systems, it is difficult to directly compare migration times. However, the matrix of choice for many microchannel studies, 4% LPA, results in the longer migration times than the pDMA matrices used here, under the same electrophoresis conditions.

DNA Sequencing Results

In addition to increased separation speed compared to LPA, pDMA can act as a self-coating matrix eliminating the need to covalently coat the channel walls, which can be expensive and time-consuming. Dynamically adsorbed polymeric wall coatings are more attractive than a covalent coating for high throughput environments due to their reduced cost and simpler implementation. The pDMA coating, however, is somewhat hydrophobic and is likely to interact with the analyte. The hydrophilic character of pHEA makes it an excellent wall coating since it can reduce electroosmotic flow and analyte-wall interaction.

Sequencing results for the various concentrations of pDMA and the commercially available Pop-5™ and Beckman LongRead™ matrices are presented in Table 2 along with the results using different dynamic coatings. The chemistry of the polymer coating greatly influences the read length. For the 4% pDMA matrix, using pDMA as a dynamic coating can achieve read lengths of 420 bases. When pHEA is applied as the dynamic coating the read length is extended by 130 bases. This increase in read length is attributed to the reduction of wall-analyte interactions that can increase band-broadening during the separation.

TABLE 2

DNA sequencing results on glass microchips

| Sequencing Matrix | Coating Polymer | Average Read Length[a] (n = 3) | Long Read Length[a] | Time[b] (s) |
|---|---|---|---|---|
| 3% pDMA | pHEA | 349 | 377 | 225 |
| 4% pDMA | pHEA | 512 | 550 | 340 |
| 5% pDMA | pHEA | 489 | 530 | 388 |
| Pop-5 ™ | pHEA | 384 | 430 | 355 |
| LongRead ™ LPA | pHEA | <300 | 318 | N/A[c] |
| 4% pDMA | pDMA | 372 | 420 | 290 |
| Pop-5 ™ | Pop-5 ™ | <50 | N/A[c] | N/A[c] |

*All runs conducted at 50° C. and 235 V/cm (~3 μA current)
[a]At 98.5% accuracy
[b]Time to reach average read length
[c]Could not be determined Another interesting result is that the Pop-5™ polymer cannot be used as a self-coating matrix in contrast to its commercial use in ABI CAE instruments. This might be explained by a fundamental difference between the glass chemistry used to fabricate the microfluidic chips in this study and the fused silica glass used in capillaries. The presence of salts and other impurities that increase the bonding properties of glass chips glass could alter the coating ability of the Pop-5™ polymer. When pHEA, however, is applied prior to Pop-5™ matrix loading into the chip, the read length is increased from very low reads (<50 bases) to approximately 380 bases. Comparing the results for the pDMA matrices with the Pop™ matrix demonstrates that polymer matrices developed for capillary systems are not necessarily the best matrices for microchannel systems. This result is further confirmed by the better sequencing read lengths obtained in the pDMA matrices versus the Beckman LongRead™ matrix, an optimized LPA matrix for capillary systems.

The combination of optimal formulations of pDMA sequencing matrix with the pHEA dynamic coating deliver longer read lengths than the commercial matrices in a shorter time. The 4% pDMA matrix delivered an average of 512 bases at 98.5% accuracy including a long read of 550 bases. Comparing different pDMA concentrations reveals that the 3% pDMA matrix results in a 25% improvement in migration time for the 500 base fragment in ssDNA separations; however, only 349 bases could be accurately called on average for sequencing. Thus, for longer read lengths, concentrations greater than 3% for this particular pDMA molar mass are required. However, the 4% formulation represents an optimal concentration, as the read lengths decrease at a concentration of 5%.

Figure 3:
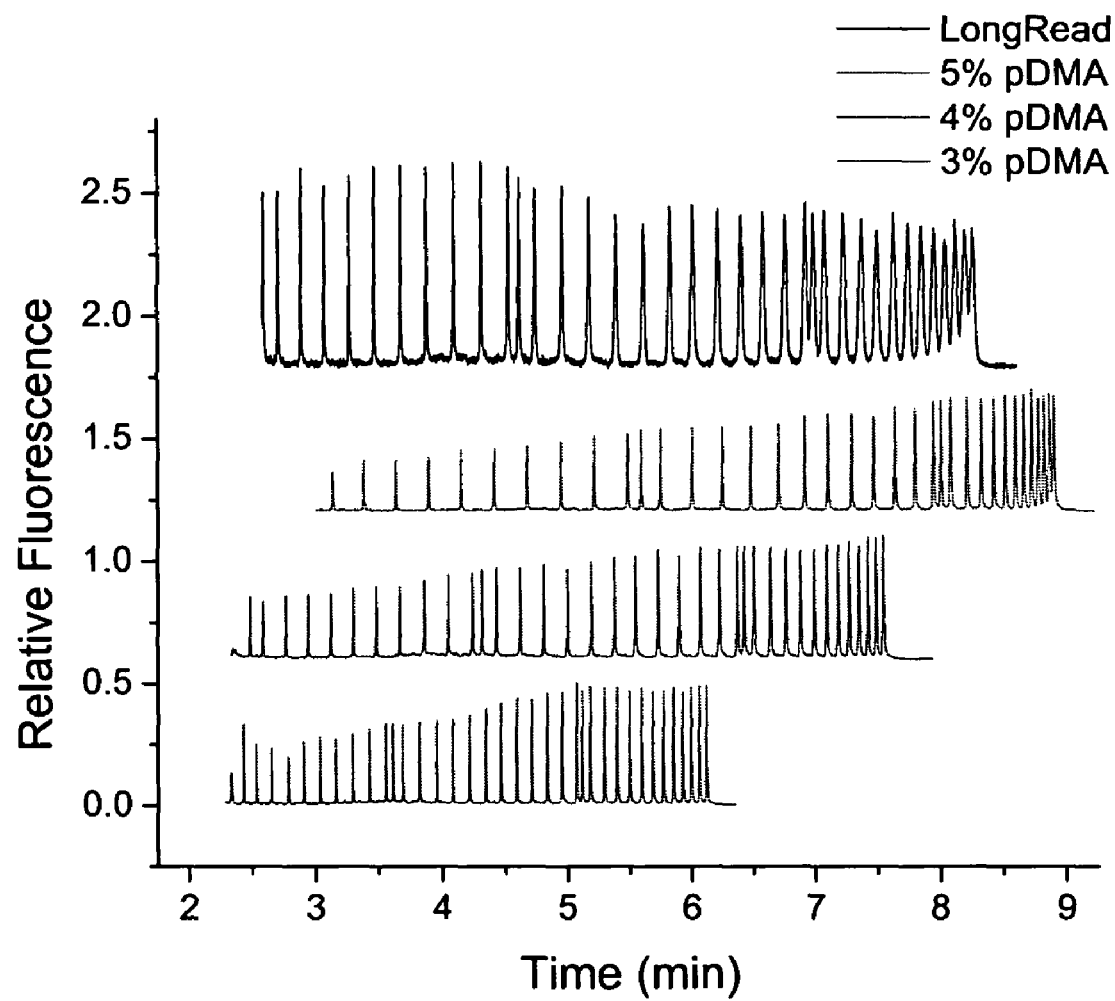
FIG. 3. ssDNA separations for pDMA matrices compared to a prior art LPA matrix. All 37 peaks were resolved for 3% and 4% pDMA. Loss of resolution was observed for 5% pDMA and the LPA matrices. The DNA fragment migration times are dependent on concentration.

From the separations in FIG. 3, the 3% pDMA matrix separated large DNA fragments quickly and with high resolution, but did not obtain sequencing read lengths comparable to the higher pDMA concentrations. As higher polymer concentration is an important parameter for separating short DNA fragments, and lower concentrations favor separating larger fragments, polymer matrices were formulated by blending polymers with high average molar mass and low average molar mass. Table 3 shows the results of two "blends" of pDMA polymers (at 98.5% accuracy). The pDMA with high average molar mass (3.4 MDa) was used at a concentration of 3% (w/v) while the lower average molar mass pDMA (240 kDa) was used at both 1% and 2% (w/v) so that the total pDMA concentrations for the two matrices were 4% and 5% (w/v). Although the matrices with a single average molar mass perform very well, the mixed molar mass matrices perform even better. The 4% blended matrix had the highest average read length at 560 bases (with a long read of 587 bases in 6 minutes), while the 5% blended matrix achieved the longest individual read at 601 bases, taking only 6.5 minutes to achieve. (The four-color sequencing electropherogram for the longest sequencing run is not shown.)

The separations in pDMA matrices and the LongRead™ LPA matrix can be further analyzed to determine the source of the poorer performance of this commercial matrix. From the ssDNA separations, both the separation selectivity and the peak widths are plotted for the various DNA fragment sizes in FIGS. 4A-B. The selectivity is a metric of the separation power of the matrix, defined as the difference in mobilities between adjacent peaks normalized by their average mobility. The peak width measures the combined effect of all band broadening sources in the system. From FIG. 4A, it is apparent that the selectivities of the 4% pDMA polymers and the LongRead™ matrix are similar and cannot explain the difference in sequencing performance. However, FIG. 4B shows that at DNA sizes greater than approximately 250 bases, there is a large increase in the peak widths in the LPA based matrix. It is believed that this band broadening effect is the main cause of poor performance in this system and that the much higher peak efficiencies (smaller widths) in the pDMA matrices result in the increased sequencing read lengths of these polymers. Furthermore, the wider peaks of the LongRead™ LPA system will probably require much longer separation channels to achieve similar read lengths (which also will require longer times).

TABLE 3

Sequencing comparison of blended molar mass pDMA matrices using pHEA coatings[a]

| Sequencing Matrix[b] | Average Read Length[c] (n = 3) | Longest Read Length[c] | Time (min) |
|---|---|---|---|
| 3% high MWpDMA + 1% low MW pDMA | 560 | 587 | 6 |
| 3% high MW pDMA + 2% low MW pDMA | 542 | 601 | 6.5 |

[a]Run Conditions identical to Table 2
[b]High molar mass pDMA is 3.4 MDa; low molar mass pDMA is 240 kDa
[c]Read length at 98.5% accuracy Investigating DNA Separation Mechanisms in the pDMA Matrices DNA separation through an entangled polymer solution is believed to proceed via two the mechanisms described above. While small DNA fragments tend to sieve through the polymer network by Ogston sieving, DNA reptation is the separation mechanism for larger fragments. Reptation provides higher resolution separations and should be the desired mechanism for high performance sequencing. This can explain why higher concentrations are needed to sequence smaller DNA sizes, since the smaller mesh sizes at higher concentrations shifts the reptation mechanism start point to smaller DNA sizes. Similar reasoning can explain why lower concentrations are needed for longer reads. As the mechanism shifts to oriented reptation, all resolving power in the matrix is lost. Since this transition depends on the mesh size (see Eq 8) DNA tends to be oriented at smaller sizes for higher polymer concentrations.

When plotting the mobility of DNA versus the fragment size on a logarithmic scale, separation by un-oriented reptation can be observed in the linear portion of the data, as shown in FIG. 5 for the separation of the ssDNA ladder from FIG. 1. The data presented in FIG. 5 is similar to data presented earlier for pDMA matrices in capillary systems. In particular, smooth transitions exist between Ogston-type sieving to unoriented reptation and for the transition from unoriented reptation to oriented reptation.

For long DNA sequencing reads, the extension of the linear region of the plots in FIG. 5 to higher DNA sizes can be important. The mobilities in 4% pDMA matrix remain in the linear region for larger DNA sizes relative to the 5% pDMA, so that the transition to oriented reptation is shifted to smaller DNA sizes. Thus, the 4% pDMA should give longer read lengths than the 5% matrix, and the results in this study show that even for DNA sizes below this limit, the 4% matrix provides better sequencing results. It should be noted, however, that the mobility plots do not account for band broadening effects that may reduce single-base resolution needed for sequencing, so sequencing read lengths are less than might be expected just from the mobility plots of the ssDNA ladders.

Entangled Network Rupture

The 3% pDMA matrix shows a linear region for the mobility plot that extends further than the two higher concentrations, yet the read lengths for this matrix are generally much lower. One reason for this is that higher polymer concentrations are needed for better separation of small DNA sizes as discussed above. Another factor influencing the separation performance for larger DNA sizes is the strength of the entanglements of the polymer network. Generally, at a given molecular weight, the strength of the entangled network increases as the polymer concentration is increased and the chains are better entangled, thus higher molar mass polymers are more effective when mesh size needs to be large to sequence larger DNA sizes. Entanglement strength is also affected by the coil size of the individual chains. pDMA chains generally have smaller coil sizes than more hydrophilic polymers such as LPA.

Strongly entangled networks are needed to separate DNA by reptation, and thus disruptions in the polymer network by migrating DNA should tend to reduce separating power and read lengths. In weakly entangled networks, disruptions are more frequent, especially by larger DNA. However, the phenomenon of DNA molecules entangling with the polymer chains as the network is broken apart would still tend to be size-dependent. This mechanism is related to transient entanglement coupling (TEC), a phenomenon well understood and established in the art, discovered by Barron et al. for the separation of dsDNA in dilute polymer solutions. (See, e.g., Barron, A. E., Soane, D. S. & Blanch, H. W. (1993) *J. Chrom. A* 652: 3-16; Barron, A. E., Blanch, H. W. & Soane, D. S. (1994) *Electrophoresis* 15: 597-615; and Barron, A. E., Sunada, W. M. & Blanch, H. W. (1996) *Biotech. Bioeng.* 52: 259-270, each of which is incorporated herein by reference in its entirety.) It is possible, then, that although un-oriented reptation is the dominant mechanism of DNA separation in these matrices, network disruption and DNA-polymer entanglement is also contributing to the separation. Since this network disruption with hooking is expected to be faster than reptation, this mechanism may account for the increased speed of separation in a more weakly entangled solution of pDMA compared to LPA sequencing matrices.

Figure 6:
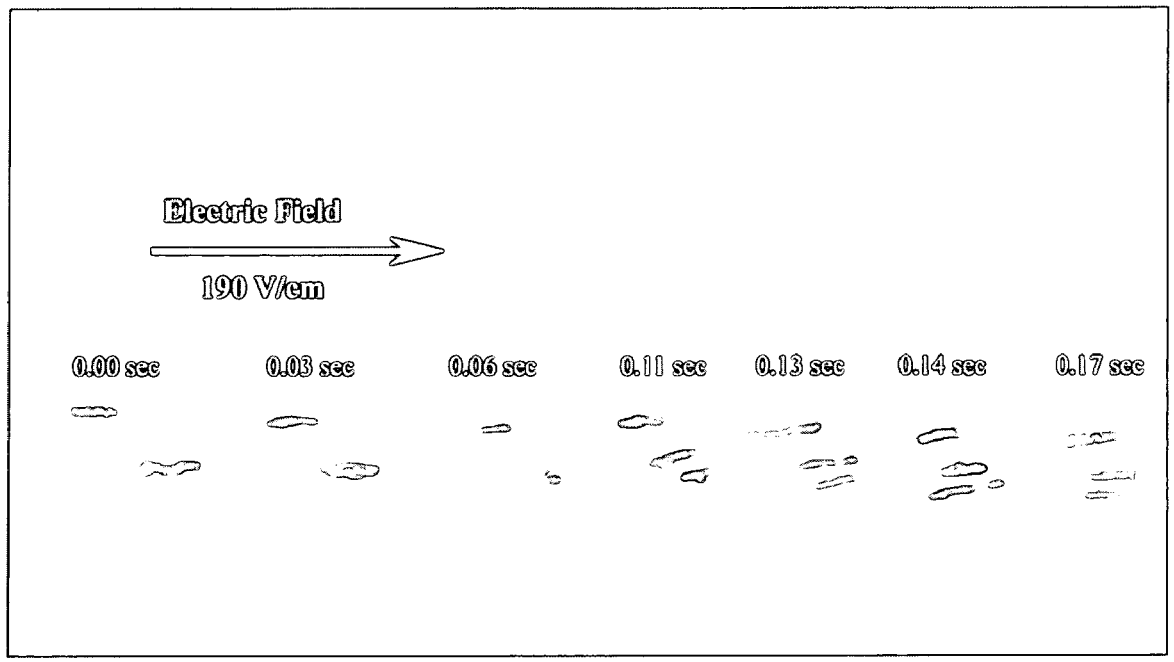
FIG. 6. Digital images captured from DNA imaging videos. A series of frames at the shown time intervals show two DNA molecules moving through a representative network of this invention. The top molecule reptates through the entire viewing frame in the given time. The lower molecule is reptating at first and then hooks and drags the polymer network through the viewing frame in a mechanism similar to transient entanglement coupling.

This hybrid mechanism of DNA separation is further suggested by videomicroscopy studies of dsDNA in the pDMA matrices. FIG. 6 shows the time evolution of two DNA molecules in a 3.0% pDMA matrix at 25° C. where one molecule is migrating via reptation while the other molecule has broken the network and is dragging polymer chains through the solution. The lower DNA molecule is reptating through the solution and then hooks onto the network and drags it along while the upper DNA molecule continues to reptate for the duration of the frame series. This demonstrates that these two mechanisms can occur simultaneously in the same matrix.

As shown below, a novel polymer matrix/polymer wall coating system for capillaries and microchips, comprising the combination of a hydrophobic polymer, e.g., poly(N,N-dimethylacrylamide) as a DNA separation matrix with a hydrophilic polymer, e.g., poly(N-hydroxyethylacrylamide) as a hydrophilic dynamic wall coating, results in an ultra-fast separation of DNA sequences by capillary and especially, microchip electrophoresis. The combination of a hydrophobic sequencing polymer along with a dynamic, hydrophilic polymer wall coating has not previously been demonstrated on a microfluidic electrophoresis device. Sequencing of 500 to 600 bases, with high accuracy of base-calling, can be achieved in less than 7 minutes specifically by the combination of two such polymers on a microchannel electrophoresis format with an effective separation distance of just 7.5 cm and other conditions such as (optimally) applied electric field strength (e.g., 235 V/cm) and temperature (e.g., 50° C.). PDMA, optimally at a Mw of about 3- about 4 MDa, dissolved to a concentration of 3-5% w/v in a 1×TTE+7 M urea buffer provides a sequencing matrix while a pHEA dynamic coating is pre-applied for application in microfluidic chips Additionally, adding between about 1 and about 2% low-molar mass pDMA (~200-300 kDa) to 3% (w/v) high-molar mass pDMA (3-4 MDa) solutions (total polymer concentration 4% (w/v)) results in even longer sequencing reads of up to 600 bases in 6.5 minutes of electrophoresis. Specifically, without limitation to any one theory or mode of operation, such conditions provide ultra-fast sequencing of DNA via a hybrid DNA separation mechanism somewhere between transient entanglement coupling and reptation, which has never been demonstrated as a mechanism for the sequencing of DNA. The mechanism can be deduced by looking at a log-log plot of DNA mobility versus fragment size, and is corroborated by single-molecule epifluorescent microscopic imaging experiments. On the log-log plot of DNA mobility vs. DNA size, the slope of the linear region under ultra-fast sequencing conditions is between −0.40 and −0.60.

Further optimization of such separation media with respect to polymer properties such as molecular weight, composition, and solution concentration, as well as optimization of the wall-coating polymers, can allow for even longer reads at this reduced time. The results obtained represent the fastest sequencing time for such a long read reported to date, and hence provide a step forward in the development of microchannel-based sequencing technologies.

EXAMPLES OF THE INVENTION

The following non-limiting examples and data illustrates various aspects and features relating to the compositions, systems, methods and/or apparatus of the present invention, including the use of hydrophobic separation matrix polymer components and hydrophilic wall coating polymer components, for microchannel electrophoresis. In comparison with the prior art, the present compositions, methods, systems and/or apparatus provide results and data which are surprising, unexpected and contrary thereto. While the utility of the invention is illustrated through the use of several polymeric components, compositions and apparatus which can be used therewith, it will be understood by those skilled in the art that comparable results are obtainable with various other polymeric components, compositions and apparatus, as are commensurate with the scope of this invention.

Example 1

PDMA Synthesis

The high-molecular weight pDMA separation matrix polymers were synthesized from the monomer N,N-dimethylacrylamide, purchased at 99+% purity from Monomer-Polymer & Dajac Labs (Feasterville, Pa. USA). A 4 wt % solution of the monomer in DI water was degassed with flowing $N_2$ for 30 minutes in a water bath set to 47° C., followed by initiation with V-50 (2,2'-azobis(2-amidinopropane) dihydrochloride, Wako Chemicals, Richmond, Va. USA). After 16 hours, the viscous polymer solution was transferred to 100,000 MW cutoff dialysis membranes where they were dialyzed with frequent water changes for 10 days. Following dialysis, the samples were lyophilized to recover the solid pDMA polymer, with a molar mass in excess of 1 MDa. Various other matrix polymers and copolymers of this invention are either commercially available or can be prepared in analogous fashion from the corresponding monomers, as described above, or by using known synthetic techniques or modifications thereof as would also be known to those skilled in the art made aware of this invention.

Additionally, adding 5 mL isopropyl alcohol to the reaction mixture described above, reduces the molar mass of pDMA suitable for blending into mixed molar mass matrices. By including 5 mL isopropyl alcohol into the monomer solution, polymerization and purification result in a polymer product with a molar mass of about 200 to about 300 kDa.

Example 2 pHEA Synthesis

To synthesize the wall-coating polymer, pHEA, the N-hydroxyethylacrylamide monomer was purchased as a 45% solution from Cambrex (sold under trade name Duramide™). Some of the monomer solution was diluted to a volume of 100 mL so that the final concentration of the monomer was 0.5 wt %. The monomer solution was degassed under $N_2$ for 30 minutes in a water bath set to 25° C. Following degassing, the reaction was initiated by adding 100 uL of a 10 wt % ammonium persulfate solution (Amresco Inc, Solon, Ohio USA) and 10 uL of TEMED (Amresco). The reaction proceeded for 16 hours after which the polymer solution was transferred to 100,000 MW cutoff dialysis membranes where it was dialyzed with frequent water changes for 10 days. Following dialysis, the solutions were lyophilized to recover the solid polymer, with a molar mass in excess of 1 MDa.

Example 3

Polymer Molecular Weight Characterization

Molecular weight distributions were determined by tandem gel-permeation chromatography-multi angle laser light scattering (GPC-MALLS). The dilute polymer solutions were first fractionated on the GPC (Waters Corp, Milford, Mass. USA) using Shodex OH-Pak columns SB-806 HQ, SB-804 HQ, and SB-802.5 HQ connected in series. After fractionation, the effluent from the GPC flows directly into the DAWN DSP laser photometer and then into the Optilab DSP interferometric refractometer (both instruments are from Wyatt Technologies, Santa Barbara, Calif. USA). During characterization, 100 uL of dilute (1 mg/mL) solution (with a mobile phase consisting of 0.1 M NaCl, 50 mM $Na_2HPO_4$, and 200 ppm $NaN_3$) is injected into the instruments and flows through at 0.300 mL/min. GPC-MALLS data were processed using ASTRA software from Wyatt Technologies. The polymers synthesized were all characterized by molar mass, radius of gyration and polydispersity index.

Example 4

Applying the pHEA Coating

Following the protocol described by Albarghouthi et al the microchannel is first filled with 1 M HCl solution and left for 15 minutes. Following the removal of the 1 M HCl solution, the channel is rinsed with de-ionized water and then filled with the pHEA coating solution and left for 15 minutes. The pHEA coating solution is a 0.1% w/v aqueous solution of the polymer in de-ionized water. The coating results in channels that give an electroosmotic flow of less than $1 \times 10^5 cm^2/Vs$.

Example 5

Microchannel/Microchip Electrophoresis

Analysis of ssM13mp 18 sequencing fragments and ssDNA ET-900 ladder (both Amersham Biosciences, Piscataway, N.J. USA) was carried out on a microchannel electrophoresis system that was custom-built for our laboratory by ACLARA Biosciences (Mountain View, Calif. USA). This system allows sensitive multi-color detection through laser-induced fluorescence (LIF). The system is comprised of two subsystems; an electrical system supplies voltage to the microfluidic device, and an optical subsystem that allows detection of fluorescent molecules as they pass the point in the channel the laser is focused. These two subsystems can both be controlled using a single program written in LabView software.

Example 6

The electrical system is powered by a high voltage power supply that allows independent control of the four electrodes. Each electrode can be set from between 0 and 4.5 kV or can be disconnected from the circuit ("floated"). The software allows the user to set the voltage of all four electrodes to the desired voltage set point for a set duration, and multiple voltage and time steps can be used sequentially for complex chip functions or different separation strategies. The optical subsystem is comprised of a confocal, epifluorescence system where fluorophores are excited by a JDS Uniphase Series 2214-30sl single-line, 488-nm argon ion laser (San Jose, Calif. USA). Mirrors are used to direct the laser beam into a TE200 inverted, epifluorescence microscope. The beam is then passed through a band-pass filter, and is reflected off of a dichroic mirror and focused through a Nikon 10×/0.45 microscope objective into the center of the microfluidic channel producing a laser spot approximately 10 μm in diameter. The emitted fluorescence is collected through the same objective and is passed through the dichroic mirror, followed by a second, wide-band-pass filter (Chroma Technology, Brattleboro, Vt. USA). The spectrum of the filtered light is measured by directing it through a transmission grating and focusing it onto a high quantum-efficiency, 532×64 pixel charge-coupled device (CCD) cooled to −15° C. (Hamamatsu Corp., Brigewater, N.J. USA). Pixel binning is applied to the data from the CCD camera to quantify the intensity of the emission over a particular range of wavelengths, calibrated by Raman scattering lines of solvents. Data collection can be accomplished at rates from 10 to 50 Hz. The CCD output is collected, binned, low-pass filtered, and stored using a program written in LabView.

Example 7

Experiments were conducted using single channel glass microchips with 7.5-cm effective separation distance purchased from Micronit Microfluidics BV (Enschede, The Netherlands). Channels were coated with either pDMA or pHEA by first rinsing with 1 M HCl for 15 minutes followed by filling the channel with a 0.1% (w/v) polymer solution for 15 minutes. Separations of ssDNA and sequencing were carried out in pDMA ($M_w$=3.4 MDa) and LPA ($M_w$=2.5 MDa) matrices with concentrations ranging from 3-5% (w/v) in TTE buffer (50 mM Tris, 50 mM TAPS, and 2 mM EDTA) with 7M urea, Pop-5™ matrix (Applied Biosystems, Inc. Foster City, Calif. USA) and Beckman LongRead™ LPA matrix (Amersham). For each run, a 235 V/cm electric field is applied for 60 seconds prior to sample injection. Also, mixed molar mass pDMA matrices were formulated with 1% or 2% of a low molar mass pDMA (about 200- about 300 kDa) and 3% to 4% of high molar mass pDMA. An offset T injector with 100 μm offset was used and the sample was injected for 40 seconds at 100 V/cm. Separation was carried out at 235 V/cm with 38 V/cm back biasing applied to the sample and sample waste wells. The chip was maintained at 50° C. for the duration of the run. Basecalling was completed using NNIM Basecaller (NNIM, LLC, Salt Lake County, Utah USA) and Sequencher v 4.0.5 (Gene Codes Corp., Ann Arbor, Mich. USA). Such pDMA matrices resulted in sequencing read lengths of about 500 to about 600 bases in 6-7 minutes, whereas commercial matrices do not sequence more than about 400 bases.

Example 8

Rheology

The zero-shear viscosity was determined using an Anton Paar Physica MCR 300 (Ashland, Va., USA) with the temperature maintained by a peltier controller connected to a digitally controlled recirculating water bath (Julabo USA Inc., Allentown, Pa., USA). Controlled shear stress and shear rate sweeps were performed with a cone-and-plate (model CP50-1) fixture and a double gap Couette (model DG26.7) fixture over a 25-50° C. temperature range. Zero-shear viscosity versus polymer concentration curves were created using this instrument. (See, FIG. 2.)

Example 9

Video Microscopy

DNA was fluorescently labeled with YOYO-1 (Molecular Probes, Eugene, Oreg. USA). All protein and sugar reagents were purchased through Fisher Scientific (Pittsburgh, Pa. USA), 48 kbp ds-λ DNA was purchased through Invitrogen (San Diego, Calif. USA) and betamercaptoethanol (BME) was purchased through (Sigma-Aldrich, St. Louis, Mo. USA). The labeling method yielded approximately one label per 5-10 base pairs of dsDNA. To observe the fluorescently labeled DNA, the stained solution was combined with catalase stock solution, glucose oxidase stock solution, BME, 20% glucose buffer, and polymer solution which had been mixed for 24 hours to allow for solvation. After gentle mixing overnight, the polymer/DNA solution was ready to be imaged.

Example 10

The hybrid chip used to image the DNA was composed of a Sylgard 184 poly(dimethylsiloxane) (Fisher Scientific, Pittsburgh, Pa. USA) microchannel and a 1.5-thick glass cover slip (Fisher Scientific, Pittsburgh, Pa. USA). The PDMS channel was formed by mixing pre-polymer and curing agent at a 10:1 ratio by weight. The degassed mixture was poured onto narrow strips of Scotch Magic Taper™ and allowed to cure in a vacuum chamber overnight. The cured PDMS was cut into 0.5 cm length squares to fit onto a cover slip and the resulting channels had depths of approximately 50 to 60 microns.

Example 11

DNA migration was visualized using a homebuilt system modeling the Morris lab at the University of Michigan. (Albarghouthi, M. N., Stein, T. M. & Barron, A. E. (2003) *Electrophoresis* 24: 1166-1175; de Carmejane, O., Yamaguchi, Y., Todorov, T. I.& Morris, M. D. (2001) *Electrophoresis* 22: 2433-2441.) The imaging system consists of a Nikon TE200 (Nikon Instruments Inc., Melville, N.Y., USA) inverted epifluorescence microscope outfitted with a Nikon CFI 100×/

N.A. 1.4 oil immersion microscope objective. DNA fluorescence was achieved using a 100 watt mercury lamp light source focused through a heat absorbing filter in sequence with a blue light excitation filter cube (460 nm-500 nm) (Chroma Technology, Brattleboro, Vt. USA). Emitted fluorescence from the DNA was collected with a 0.5 inch CCD, TM-67 10-CL camera (JAI Pulnix, Sunnyvale, Calif. USA) through a 510 nm long pass filter (Chroma Technology, Brattleboro, Vt. USA) and a VS4-1845 Generation 3 image intensifier (Videoscope International, Dulles, Va. USA). The high-speed camera has an adjustable frame rate capable of 120 frames/sec with a full spatial resolution of 648×484 pixels. All videos were captured at 30 frames/sec directly to computer via a PIXCI control board (EPIX INC., Buffalo Grove, Ill. USA) utilizing the XCAP-STD (EPIX INC, Buffalo Grove, Ill. USA) software. Electrophoresis voltages were achieved using high voltage power supply from Micronit. Single DNA molecules migrating through the polymer matrices can be imaged using this technique.

Example 12

Using a microchannel pre-coated with a dynamic pHEA polymer, a 4% (w/v) poly(N-methoxyethylacrylamide) (PN-MEA) polymer solution was loaded into the channel as the sequencing matrix. When the temperature is set at 50° C. and with an electric field of 235 V/cm in the 7.5 cm long-separations channel, DNA sequencing read lengths of 540 bases can be achieved at 98.5% accuracy in about 6.5 minutes. Basecalling was performed by NNIM basecaller and Sequencer version 4.0.5. (The sequencing electropherogram is not shown.)

Example 13

In addition to sequencing DNA on microchips, the polymer systems of this invention (e.g., pDMA matrix and pHEA dynamic coating) has also been used in 22-cm capillaries on an ABI 3100 commercial apparatus. All sequencing runs were carried out at a temperature of 50° C. and an electric field of 250 V/cm. The raw sequencing data shows that the 4% mixed molar mass pDMA (1% low molar mass and 3% high molar mass) allows rapid sequencing versus commercially available POP™-6 matrix. The separation in such a pDMA matrix is 3 times faster than in the POP™ matrix demonstrating that more rapid sequencing is also possible in capillary instruments. The sequencing results are shown in Table 4, comparing the 4% mixed molar mass pDMA and POP™-6 both in pHEA coated capillaries. The separation is much faster in the mixed molar mass pDMA. This matrix sequenced 650 bases in about 22 minutes. Basecalling was completed using NN1M basecaller and sequencer version 4.0.5 (The sequencing electropherogram for the 4% mixed molar mass is not shown.)

TABLE 4

Comparison of sequencing matrices

| Polymer | Coating | AVG READ LENGTH (n = 4) | Long Read Length | Time (min) |
|---|---|---|---|---|
| 4% pDMA* | pHEA | 650 + 10 | 660 | 22 |
| POP-6 | pHEA | 677 + 68 | 757 | 60 |

*3% high molar mass (2.7 MDa) + 1% low molar mass (280 kDa)

As demonstrated by the preceding examples, DNA sequencing up to 600 bases was demonstrated in 6.5 minutes using a pDMA matrix with a pHEA dynamic coating. The pDMA synthesized for this work performed much better than the commercially available matrices, and the choice of the pHEA over more hydrophobic coatings is critical for extending read lengths. Single stranded DNA fragments possess higher mobilities in the pDMA matrices used in this study than in the typical LPA matrices used in previous microchannel studies. The fact that the pDMA matrices allow sequencing read lengths longer than 600 bases in only 7.5 cm of separation distance also contribute to the high speed.

Rheology data and videomicroscopy studies suggest that weakly entangled pDMA networks may allow faster sequencing than more entangled networks since the migrating DNA molecules may disrupt the network more frequently. Although network disruptions generally lead to lower separation ability, the DNA can hook and drag the loose polymer chains, which is similar to the TEC mechanism where DNA mobility is still size-dependent. While this hybrid separation mechanism is suggested by videomicroscopy, no current theory for DNA separation takes these mechanisms into account concurrently.

This system can be optimized, and the analysis of mobility versus DNA size suggests that longer read lengths are possible. Sequencing has been demonstrated in both 11.5 cm and 15.9 cm channel lengths. Assuming a diffusion-limited system, the minimum resolution where the basecaller can accurately call bases scales with the square root of the channel length, while the migration time should increase linearly. Therefore, using an 11.5 cm channel, this system can be used to produce up to a 630 base read in ~9 minutes while a 15.9 cm channel will produce an 800 base read in ~12 minutes. Such results will be tempered by the transition to oriented reptation begins near 850 bases for the 4% pDMA matrix, which will change the mobility dependence on length and shorter reads may be expected. Nevertheless, the ability of the pDMA matrix along with the pHEA dynamic coating to provide long sequencing reads at shorter times represents a significant step forward for microchip sequencing systems and will advance the development of the next generation of sequencing technologies.

The systems/compositions of this invention can extend to sequencing centers or other sequencing applications where a linear polymer matrix and dynamic polymer coating could be used. Many genotyping and forensic applications such that require DNA separation by electrophoresis may also be interested since a wide range of DNA sizes can be resolved, for instance, with the matrix and coating combination as shown in FIG. 1A.

We claim:

1. A DNA sequencing or genotyping composition for microchannel electrophoresis comprising a hydrophobic separation matrix component comprising a polyacrylamide of a formula $-[CH_2C(R)C(O)NR'R'']_{\overline{n}}$, wherein R is selected from H and methyl, and R' and R'' are independently selected from $C_1$ to about $C_8$ linear alkyl moieties $C_1$ to about $C_8$ alkoxy-substituted linear alkyl moieties, $C_1$ to about $C_8$ branched alkyl moieties and $C_1$ to about $C_8$ alkoxy-substituted branched alkyl moieties, and copolymers thereof, said polyacrylamide at least partially water soluble; and a hydrophilic wall coating component comprising a poly(N-hydroxyethylacrylamide).

2. The composition of claim 1, wherein said matrix component is selected from poly(N,N-dimethylacrylamide) and a poly(N,N-dimethylacrylamide) copolymer.

3. The composition of claim 2, wherein said matrix component comprises about 3% (w/v) to about 5% (w/v) poly(NN-dimethylacrylamide) in an aqueous medium.

4. The composition of claim 3, wherein said matrix component comprises about 3% (w/v) poly(N,N-dimethylacrylamide), with a weight average molar mass ranging from about 3 to about 5 MDa.

5. The composition of claim 3, wherein said matrix component comprises about 1% (w/v) to about 2% (w/v) poly(NN-dimethylacrylamide), with a weight average molar mass ranging from about 200 to about 300 kDa.

6. A sequencing composition comprising a hydrophobic separation matrix component comprising a poly(N,N-dimethylacrylamide) component and a wall coating component comprising a hydrophilic poly(N-hydroxyethylacrylamide) component.

7. The composition of claim 6, wherein said matrix component comprises about 3% (w/v) to about 5% (w/v) poly(N,N-dimethylacrylamide) in an aqueous medium.

8. The composition of claim 7, wherein said matrix component comprises about 3% (w/v) poly(NN-dimethylacrylamide), with a weight average molar mass ranging from about 3 to about 5 MDa, and about 1% (w/v) to about 2% (w/v) poly(N,N-dimethylacrylamide), with an average molar mass ranging from about 200 to about 300 kDa.

9. A microchannel electrophoresis system for DNA and RNA separations, said system comprising a hydrophobic separation matrix component comprising a poly(N,N-dimethylacrylamide) and a hydrophilic wall coating component comprising a poly(N-hydroxyethylacrylamide); and a microchannel substrate selected from a micro-dimensioned capillary, said capillary defining an internal dimension ranging from about 10 microns to about 150 microns, and a microfluidic electrophoresis chip comprising a microchannel ranging from about 10 microns to about 150 microns.

10. The system of claim 9, wherein said matrix component comprises about 3% (w/v) poly(N,N-dimethylacrylamide), with a weight average molar mass ranging from about 3 to about 5 MDa, and about 1% (w/v) to about 2% (w/v) poly(N,N-dimethylacrylamide), with a weight average molar mass ranging from about 200 to about 300 kDa.

11. The system of claim 10, wherein said poly(N-hydroxyethylacrylamide) is contacted with said substrate.

12. A method of using a polymeric wall coating and separation matrix system for electrophoretic DNA and RNA separation, said method comprising:
providing a system comprising a poly(NN-dimethylacrylamide) separation matrix component comprising about 3% (w/v) to about 5% (w/v) of said system, and a poly(N-hydroxyethylacrylamide) wall coating component;
introducing said system to a substrate selected from a microchannel electrophoresis capillary and a microfluidic electrophoresis chip; and
contacting a mixture selected from DNA sequencing reaction product components and RNA components with said system, at an applied voltage and for a time at least partially sufficient for electrophoretic separation of said mixture.

13. The method of claim 12, wherein said matrix component comprises about 3% (w/v) poly(N,N-dimethylacrylamide), with a weight average molar mass ranging from about 3 to about 5 MDa, and about 1% (w/v) to about 2% (w/v) poly(N,N-dimethylacrylamide), with a weight average molar mass ranging from about 200 to about 300 kDa.

14. The method of claim 13, wherein said poly(N-hydroxyethylacrylamide) component is contacted with said substrate.

15. The method of claim 14, wherein said poly(N-hydroxyethylacrylamide) component is in an aqueous medium.

16. The method of claim 12, wherein said system comprises a DNA sequencing buffer and said mixture comprises DNA molecules.

17. The method of claim 16, separating single-stranded DNA, wherein one of said DNA sequence components comprises up to about 800 bases, said separation a function of time and microchannel length.

18. A microchannel electrophoresis apparatus comprising a substrate selected from a micro-dimensioned capillary and a microfluidic electrophoresis chip; and a polymeric system thereon, said system comprising a poly(NN-dimethylacrylamide) component as a separation matrix, said component comprising about 3% (w/v) to about 5% (w/v) of said system; and a poly(N-hydroxyethylacrylamide) component as a wall coating.

19. The apparatus of claim 18, wherein said matrix component comprises about 3% (w/v) poly(N,N-dimethylacrylamide), with a weight average molar mass ranging from about 3 to about 5 MDa, and about 1% (w/v) to about 2% (w/v) poly(NN-dimethylacrylamide), with a weight average molar mass ranging from about 200 to about 300 kDa.

20. The apparatus of claim 18, wherein said poly(N-hydroxyethylacrylamide) component is applied to said substrate.

21. A method of using a poly(NN-dimethylacrylamide) matrix to enhance DNA separation speed, said method comprising:
providing a microchannel substrate selected from a micro-dimensioned capillary and a microfluidic electrophoresis chip;
coupling a hydrophilic poly(N-hydroxyethylacrylamide) wall coating component to said substrate;
introducing a hydrophobic poly(NN-dimethylacrylamide) matrix component to said substrate, said matrix component at least partially water soluble; and
contacting a mixture of DNA sequence components and said matrix component, at an applied voltage and for a time at least partially sufficient for electrophoretic separation of said mixture, said poly(NN-dimethylacrylamide) of a molecular weight and at a concentration at least partially sufficient for at least one of transient entanglement coupling and reptation of DNA components within said mixture.

22. The method of claim 21 wherein said separation is a combination of said transient entanglement coupling and reptation.

23. The method of claim 22 wherein said DNA components migrate by transient entanglement coupling about 50% of the time of said migration and by reptation about 50% of the time of such migration.

24. The method of claim 22 wherein DNA migration dynamics are monitored by epifluorescent videomicroscopy of fluorescently stained DNA molecules.

25. The method of claim 22 wherein said matrix comprises about 3% (w/v) poly(N,N-dimethylacrylamide), with a weight average molar mass ranging from about 3 to about 5 MDa, and about 1% (w/v) to about 2% (w/v) poly(N,N-dimethylacrylamide), with a weight average molar mass ranging from about 200 to about 300 kDa.

26. The method of claim 25 wherein said migration is characterized by a linear region of a log-log plot of DNA electrophoretic mobility versus DNA molecular size through said matrix, said molecular size in one of bases and base pairs.

27. The method of claim 26 wherein said DNA molecular size ranges from about 200 bases to about 800 bases, and the linear region of said plot has a slope between about −0.40 and −0.60.

28. A method of using a hydrophobic polymer matrix to enhance DNA separation speed, said method comprising:

provid ing a microchannel substrate selected from a microdimensioned capillary and a microfluidic electrophoresis chip;

coupling a hydrophilic poly(N-hydroxyethylacrylamide) wall coating component to said substrate;

introducing a hydrophobic separation matrix component to said substrate said matrix component selected from the polyacrylamides of claim 1, copolymers thereof, combinations of said polyacrylamides, combinations of said copolymers and combinations of any of said polyacrylamides with any of said copolymers, said matrix component at least partially water soluble; and contacting a mixture of DNA sequence components and said matrix component, at an applied voltage and for a time at least partially sufficient for electrophoretic separation of said mixture, said polyacrylamide of a molecular weight and at a concentration at least partially sufficient for at least one of transient entanglement coupling and reptation of DNA components within said mixture.

29. The method of claim 28 wherein said separation is a combination of said transient entanglement coupling and reptation.

30. The method of claim 29 where said DNA components migrate by transient entanglement coupling about 50% of the time said migration and by reputation about 50% of the time of such migration.

31. The method of claim 29 wherein DNA migration dynamics are monitored by epifluorescent videomicroscopy of fluorescently stained DNA molecules.

32. The method of claim 28 wherein said matrix component is selected from poly(N,N-dimethylacrylamide) and copolymers thereof.

33. The method of claim 31 wherein said matrix comprises about 3% (w/v) poly(N,N-dimethylacrylamide), with a weight average molar mass ranging from about 3 to about 5 MDa, and about 1% (w/v) to about 2% (w/v) poly(N,N-dimethylacrylamide), with a weight average molar mass ranging from about 200 to about 300 kDa.

34. The method of claim 33 wherein said migration is characterized by a linear region of a log-log plot of DNA electrophoretic mobility versus DNA molecular size through said matrix, said molecular size in one of bases and base pairs.

35. The method of claim 34 wherein said DNA molecular size ranges from about 200 bases to about 800 bases, and the linear region of said plot has a slope between about −0.40 and −0.60.

* * * * *

UNITED STATES PATENT AND TRADEMARK OFFICE
CERTIFICATE OF CORRECTION

| | | |
|---|---|---|
| PATENT NO. | : 7,862,699 B2 | Page 1 of 2 |
| APPLICATION NO. | : 11/591915 | |
| DATED | : January 4, 2011 | |
| INVENTOR(S) | : Barron et al. | |

It is certified that error appears in the above-identified patent and that said Letters Patent is hereby corrected as shown below:

Column 1, lines 8-12:

"The United States government has certain rights to this invention pursuant to Grant Nos. 1 R01 HG 019770-01 and DMR-0076097 from the National Institutes of Health and the National Science Foundation, respectively, to Northwestern University." should read --This invention was made with government support under grant number 1 R01 HG019770-01 awarded by the National Institutes of Health and grant number DMR0076097 awarded by the National Science Foundation. The government has certain rights in the invention.--

Column 2, line 27:
"(PDMA)" should read --(pDMA)--

Column 2, line 51:
"C8" should read --$C_8$--

Column 14, line 61:
"1×105cm2/Vs" should read --1×10-5cm2/Vs--

In the claims:
Claim 3, Column 18, line 67:
"(NN-dimethylacrylamide)" should read --(N,N-dimethylacrylamide)--
Claim 5, Column 19, Line 7:
"(NN-dimethylacrylamide)" should read --(N,N-dimethylacrylamide)--
Claim 8, Column 19, line 18:
"(NN-dimethylacrylamide)" should read --(N,N-dimethylacrylamide)--
Claim 12, Column 19, line 45:
"(NN-dimethylacrylamide)" should read --(N,N-dimethylacrylamide)--
Claim 18, Column 20, line 11:
"(NN-dimethylacrylamide)" should read --(N,N-dimethylacrylamide)--

Signed and Sealed this
Eleventh Day of October, 2011

David J. Kappos
*Director of the United States Patent and Trademark Office*

Claim 19, Column 20, line 20:
"(NN-dimethylacrylamide)" should read --(N,N-dimethylacrylamide)--
Claim 21, Column 20, line 25:
"(NN-dimethylacrylamide)" should read --(N,N-dimethylacrylamide)--
Claim 21, Column 20, line 33:
"(NN-dimethylacrylamide)" should read --(N,N-dimethylacrylamide)--
Claim 21, Column 20, line 39:
"(NN-dimethylacrylamide)" should read --(N,N-dimethylacrylamide)--